United States Patent
Wada et al.

(10) Patent No.: US 11,272,833 B2
(45) Date of Patent: Mar. 15, 2022

(54) TREATMENT-INSTRUMENT INSERTION AID

(71) Applicants: KEIO UNIVERSITY, a university of Japan, Tokyo (JP); KABUSHIKI KAISHA TOP, Tokyo (JP)

(72) Inventors: Norihito Wada, Tokyo (JP); Takuya Miyazaki, Tokyo (JP); Yoshihiko Himura, Tokyo (JP)

(73) Assignees: KEIO UNIVERSITY, Tokyo (JP); KABUSHIKI KAISHA TOP, Tokyo (JP)

( * ) Notice: Subject to any disclaimer, the term of this patent is extended or adjusted under 35 U.S.C. 154(b) by 319 days.

(21) Appl. No.: 15/556,670

(22) PCT Filed: Mar. 12, 2015

(86) PCT No.: PCT/JP2015/057388
§ 371 (c)(1),
(2) Date: Sep. 8, 2017

(87) PCT Pub. No.: WO2016/143142
PCT Pub. Date: Sep. 15, 2016

(65) Prior Publication Data
US 2018/0049624 A1    Feb. 22, 2018

(51) Int. Cl.
*A61B 1/00*    (2006.01)
*A61B 1/005*    (2006.01)
(Continued)

(52) U.S. Cl.
CPC ........ *A61B 1/00154* (2013.01); *A61B 1/0055* (2013.01); *A61B 1/00135* (2013.01);
(Continued)

(58) Field of Classification Search
CPC ............ A61B 1/00135; A61B 1/00142; A61B 1/00154; A61B 1/00073; A61B 1/00087;
(Continued)

(56) References Cited

U.S. PATENT DOCUMENTS 6,099,464 A * 8/2000 Shimizu ............. A61B 1/00075
600/104
6,878,106 B1 * 4/2005 Herrmann .......... A61B 1/00073
600/104
(Continued)

FOREIGN PATENT DOCUMENTS

JP    56-89233    7/1981
JP    62-167531    7/1987
(Continued)

OTHER PUBLICATIONS

International Search Report, dated Jun. 2, 2015 (Jun. 2, 2015).
European Search Report dated Oct. 15, 2018, 7 pages.

*Primary Examiner* — Ryan N Henderson
(74) *Attorney, Agent, or Firm* — Rankin, Hill & Clark LLP

(57) ABSTRACT

A treatment-instrument insertion aid (10) for aiding insertion of a treatment instrument into a body includes an inner tube (20) having flexibility into which the treatment instrument is insertable, and an outer tube (30) having flexibility into which the inner tube (20) is insertable. Both end portions (20B) of the inner tube (20) are formed of a hard material, and an intermediate portion (20A) between both the end portions (20B) is formed of a soft material.

8 Claims, 5 Drawing Sheets

(51) Int. Cl.
*A61B 1/018* (2006.01)
*A61B 1/01* (2006.01)
*A61B 17/00* (2006.01)

(52) U.S. Cl.
CPC .......... *A61B 1/018* (2013.01); *A61B 1/00071* (2013.01); *A61B 1/00133* (2013.01); *A61B 1/01* (2013.01); *A61B 17/00234* (2013.01)

(58) Field of Classification Search
CPC .............. A61B 1/00098; A61B 1/0014; A61B 1/00147; A61B 1/01; A61B 1/0051; A61B 1/0055; A61B 1/0056; A61B 17/3417; A61B 17/3421; A61B 17/3423; A61B 17/3445; A61B 2017/3425; A61B 2017/3427; A61B 2017/3447; A61B 2017/3449; A61B 2017/345; A61B 2017/3452
See application file for complete search history.

(56) References Cited

U.S. PATENT DOCUMENTS

| | | | | |
|---|---|---|---|---|
| 7,803,137 B2* | 9/2010 | Stefanchik | ......... | A61B 1/00073 604/174 |
| 7,815,565 B2* | 10/2010 | Stefanchik | ......... | A61B 1/00135 600/121 |
| 7,976,458 B2* | 7/2011 | Stefanchik | ......... | A61B 1/00135 600/104 |
| 8,007,432 B2* | 8/2011 | Vakharia | .......... | A61B 17/00234 600/104 |
| 8,491,585 B2* | 7/2013 | Hannani | ............ | A61B 17/1671 606/80 |
| 8,911,359 B2* | 12/2014 | Nomura | ............. | A61B 1/00133 600/114 |
| 9,066,655 B2* | 6/2015 | Stefanchik | ......... | A61B 1/00147 |
| 9,254,077 B2* | 2/2016 | Soetermans | ........... | A61B 1/018 |
| 9,877,794 B2* | 1/2018 | Csiky | .................... | A61B 34/30 |
| 2002/0028984 A1* | 3/2002 | Hayakawa | ............. | A61B 1/005 600/139 |
| 2004/0162568 A1* | 8/2004 | Saadat | ............... | A61B 1/00135 606/139 |
| 2007/0106113 A1* | 5/2007 | Ravo | ..................... | A61B 1/012 600/113 |
| 2008/0132758 A1* | 6/2008 | Stefanchik | ......... | A61B 1/00073 600/104 |
| 2009/0149710 A1* | 6/2009 | Stefanchik | ............. | A61B 1/005 600/146 |
| 2009/0177041 A1* | 7/2009 | Stefanchik | ......... | A61B 17/3421 600/146 |
| 2009/0221934 A1* | 9/2009 | Kuhns | .................... | A61B 10/06 600/564 |
| 2009/0259141 A1* | 10/2009 | Ewers | ................ | A61B 1/00098 600/562 |
| 2010/0016659 A1* | 1/2010 | Weitzner | ............ | A61B 1/00073 600/104 |
| 2012/0232339 A1* | 9/2012 | Csiky | .................. | A61B 1/00135 600/104 |
| 2014/0094658 A1* | 4/2014 | Nomura | .................. | A61B 1/018 600/114 |
| 2015/0080933 A1* | 3/2015 | Igov | .................... | A61B 1/00082 606/190 |
| 2016/0174814 A1* | 6/2016 | Igov | .................... | A61B 17/0218 600/106 |
| 2017/0224378 A1* | 8/2017 | Igov | ............... | A61B 17/320016 |
| 2018/0049624 A1* | 2/2018 | Wada | ................... | A61B 1/0055 |
| 2018/0092635 A1* | 4/2018 | Csiky | ................. | A61B 17/3423 |

FOREIGN PATENT DOCUMENTS

| | | | |
|---|---|---|---|
| JP | H01-254138 A | | 10/1989 |
| JP | 2000-37390 | | 2/2000 |
| JP | 2000-166936 | | 6/2000 |
| JP | 2000-325303 | | 11/2000 |
| JP | 2003-501197 | | 1/2003 |
| JP | 2004-337617 | | 12/2004 |
| JP | 2005-046273 | | 2/2005 |
| JP | 2005-177517 | | 7/2005 |
| JP | 2010200913 A | * | 9/2010 |
| JP | 2012-200552 | | 10/2012 |
| WO | 2011/046002 | | 4/2011 |
| WO | 2014/046618 A1 | | 3/2014 |

\* cited by examiner

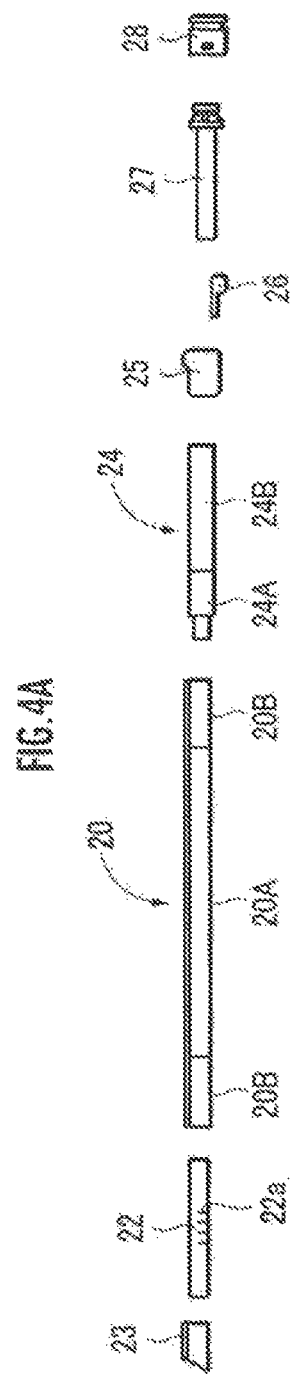

TREATMENT-INSTRUMENT INSERTION AID

TECHNICAL FIELD

The present invention relates to a treatment-instrument insertion aid for aiding insertion of a treatment instrument such as an endoscope, forceps or the like when the treatment instrument is inserted into a body.

BACKGROUND ART

In the medical field, when a treatment instrument is inserted into a body, a treatment-instrument insertion aid is used to aid the insertion of the treatment instrument.

As the treatment-instrument insertion aid, a multi-lumen tube endoscope has been hitherto known, which includes plural flexible tubes serving as inner tubes integrally fixed by a resin body. The tubes form an image guide conduit, a light guide conduit, a channel conduit for a treatment, a channel conduit for air supply/water supply or the like.

It is said that according to the treatment-instrument insertion aid, since the flexible tubes make it possible to secure the diameters and shapes of the conduits, the insertability of a treatment instrument can be enhanced when the treatment instrument is in use (see Patent Literature 1, for example).

CITATION LIST

Patent Literature

Patent Literature 1: Japanese Patent Laid-Open No. S62-167531

SUMMARY OF THE INVENTION

Technical Problem

However, the foregoing treatment-instrument insertion aid has a disadvantage that it is impossible to change the number, diameter, etc. of inner tubes.

Therefore, it is conceivable to surround the periphery of the inner tube by an outer tube having flexibility. In this case, however, when the inner tube is formed of a soft material, there occurs a disadvantage that the inner tube may be crushed. On the other hand, when the inner tube is formed of a hard material, there occurs a disadvantage that it may be difficult to bend the inner tube.

An object of the present invention is to overcome the foregoing disadvantages, and provide a treatment-instrument insertion aid that makes it difficult to crush an inner tube and can be easily bent.

Solution to Problem

In order to attain the above object, according to the present invention, a treatment-instrument insertion aid for aiding insertion of a treatment instrument into a body, comprises: an inner tube having flexibility into which the treatment instrument is insertable; and an outer tube having flexibility into which the inner tube is insertable, wherein both end portions of the inner tube are formed of a hard material, and an intermediate portion between the both end portions is formed of a soft material softer than the hard material.

According to the treatment-instrument insertion aid of the present invention, since both the end portions are formed of the hard material, the inner tube can be prevented from being crushed at both the end portions. Furthermore, since the inner tube is formed of the soft material at the intermediate portion thereof and has an easily bendable portion, the inner tube can be easily bent during hand manipulation.

In the treatment-instrument insertion aid of the present invention, it is preferable that a bendable bending member having a cylindrical shape is attached to a distal end portion of the inner tube.

In this case, the treatment instrument can be easily turned from the distal end portion of the inner tube to a desired direction.

In the treatment-instrument insertion aid of the present invention, it is preferable that the bending member is formed of a hard material same as or harder than the hard material, and partially has a thin wall part reduced in thickness.

In this case, since the bending member has the thin wall part, the bending member can be easily bent in spite of being formed of the hard material. The thin wall part may contain a space whose thickness is equal to zero.

In the treatment-instrument insertion aid of the present invention, it is preferable that a cover formed of a soft material softer than the hard material constituting the bending member is attached to a distal end portion of the bending member.

In this case, a risk of damaging tissues by the distal end portion of the bending member formed of the hard material can be prevented.

In the treatment-instrument insertion aid of the present invention, it is preferable that both end portions of the outer tube are formed of a hard material, and an intermediate portion between the both end portions has a portion formed of a soft material softer than the hard material.

In this case, since both the end portions of the outer tube are formed of the hard material, the outer tube can be prevented from being crushed at least at both the end portions. Furthermore, the inner tube in the outer tube can be also prevented from being crushed. In addition, since the outer tube is formed of the soft material and has an easily bendable portion, the outer tube can be also easily bent during hand manipulation.

In the treatment-instrument insertion aid of the present invention, it is preferable that the intermediate portion alternately has a portion formed of the soft material and a portion formed of a hard material harder than the soft material.

In this case, since a portion formed of a hard material exists in addition to both the end portions, the outer tube can be also prevented from being crushed at this portion. Furthermore, the inner tube in the outer tube can be more effectively prevented from being crushed.

In the treatment-instrument insertion aid of the present invention, it is preferable that an engaging portion is provided on an inner peripheral surface of the outer tube, and an engaged portion to be engaged with the engaging portion is provided on an outer peripheral surface of the inner tube.

In this case, the inner tube can be locked at a predetermined place on the inner peripheral surface of the outer tube, so that the interference among inner tubes can be prevented.

In the treatment-instrument insertion aid of the present invention, it is preferable that an engaged portion of a guide member extending in an axial direction from a distal end side to a proximal end side is engaged with the engaging portion with which the engaged portion of the inner tube is not engaged.

In this case, the interference among the inner tubes can be surely prevented by the guide member.

In the treatment-instrument insertion aid of the present invention, it is preferable that a plurality of engaging portions are circumferentially spaced apart from one another on an inner peripheral surface of the outer tube, engaged portions of rail members each extending in an axial direction from a distal end side to a proximal end side are engaged with the plurality of engaging portions, and an engaged portion to be engaged with an engaging portion formed between the inner peripheral surface of the outer tube and the adjacent rail members is provided on an outer peripheral surface of the inner tube.

In this case, since the inner tube can be locked at a predetermined place by using the rail members locked to the inner peripheral surface of the outer tube, the interference among the inner tubes can be prevented.

In the treatment-instrument insertion aid of the present invention, it is preferable that an engaged portion of a guide member extending in the axial direction from the distal end side to the proximal end side is engaged with the engaging portion with which the engaged portion of the inner tube is not engaged.

In this case, the interference among the inner tubes can be also surely prevented by the guide member.

BRIEF DESCRIPTION OF THE DRAWINGS

FIG. 4A is an exploded view of an inner tube, etc.

DESCRIPTION OF EMBODIMENT

A treatment-instrument insertion aid 10 according to an embodiment of the present invention will be described. The treatment-instrument insertion aid 10 is used to aid the insertion of a treatment instrument (not shown) such as an endoscope, forceps, a surgical knife or the like into a body.

Figure 1:
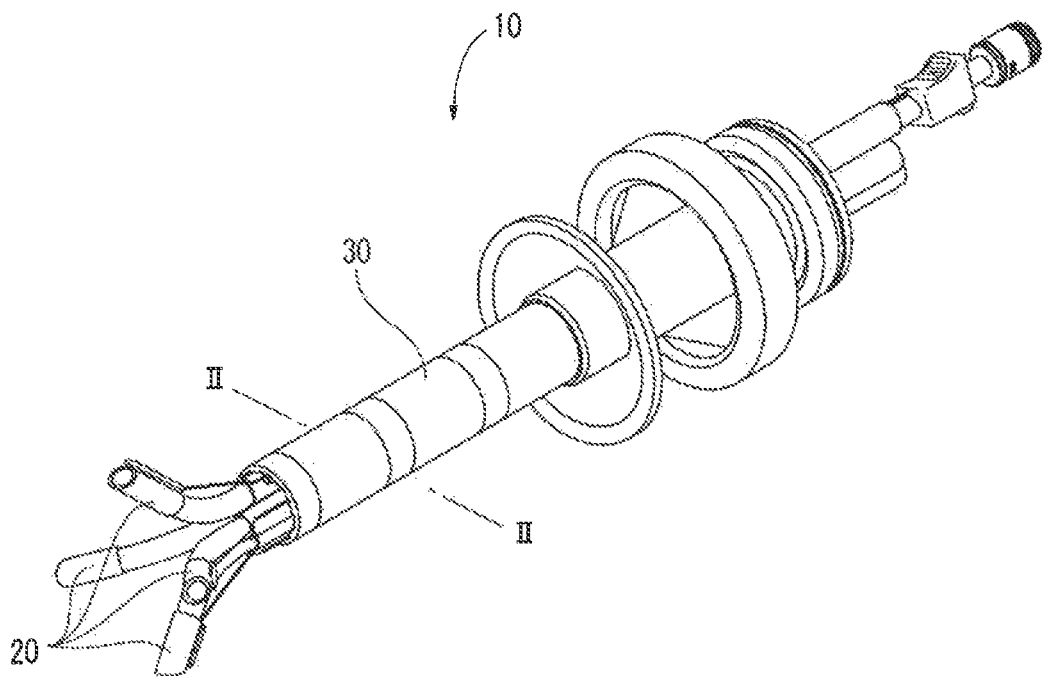
FIG. 1 is a perspective view showing a treatment-instrument insertion aid according to an embodiment of the present invention.
Figure 2:
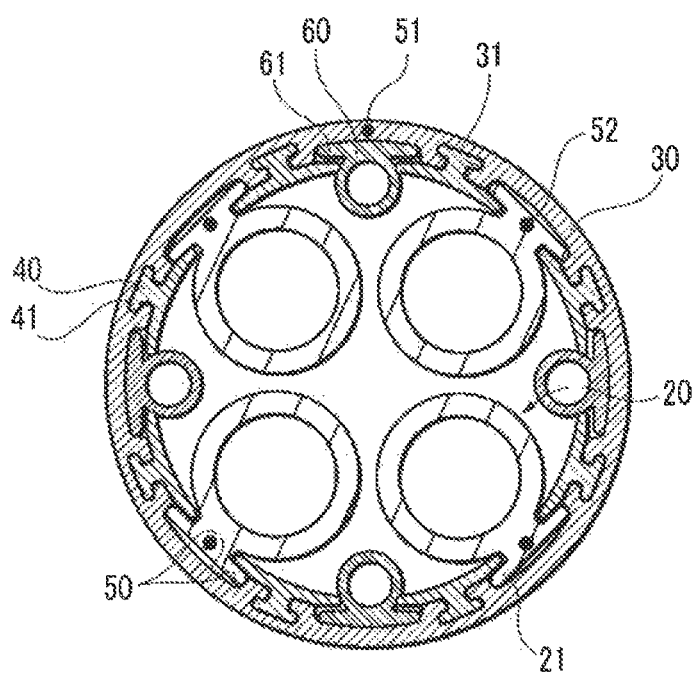
FIG. 2 is a cross-sectional view taken along an A-A line of FIG. 1.

As shown in FIGS. 1 and 2, the treatment-instrument insertion aid 10 mainly includes inner tubes 20, an outer tube 30 and rail members 40. Plural rail members 40 are fitted to the outer tube 30, and one or plural inner tubes 20 are inserted in the outer tube 30.

The outer tube 30 is a cylindrical body having flexibility, and has plural guiding portions 31 which extend in the axial direction from a distal end side to a proximal end side on the inner surface. The guiding portions 31 are dovetail grooves formed on the inner wall surface of the outer tube 30, and formed at equal intervals in the circumferential direction on the inner wall surface.

In this embodiment, as shown in FIG. 2, the dovetail grooves are formed at protruding portions protruding to the center axis, and have rectangular cross-sectional shapes at an opening portion and a back side. However, the shape of the dovetail grooves is not limited to the foregoing shape, but may be a substantially trapezoidal shape which spreads further to the back side than the opening portion, or may be rectangular at the opening portion and substantially circular on the back side or the like.

Figure 3A:
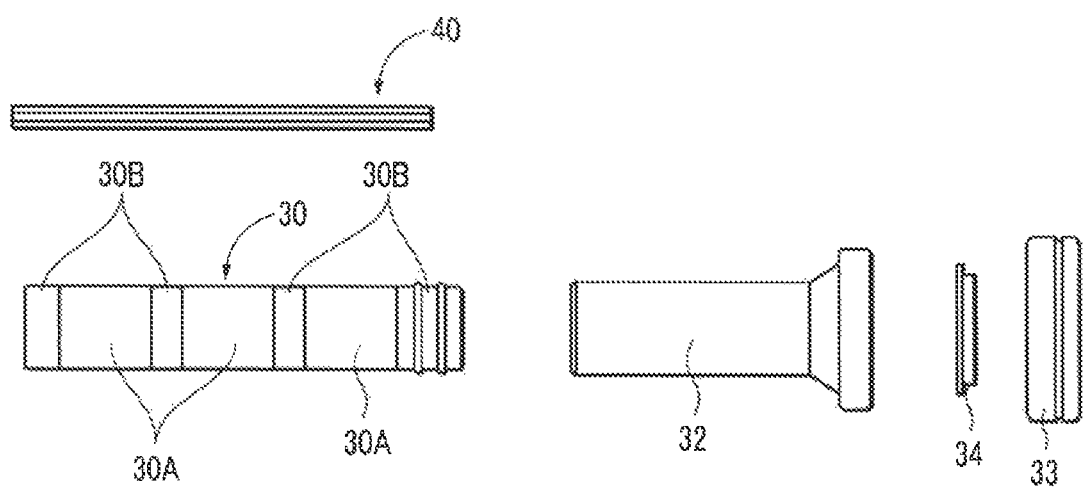
FIG. 3A is an exploded side view of an outer tube, etc.
Figure 3B:
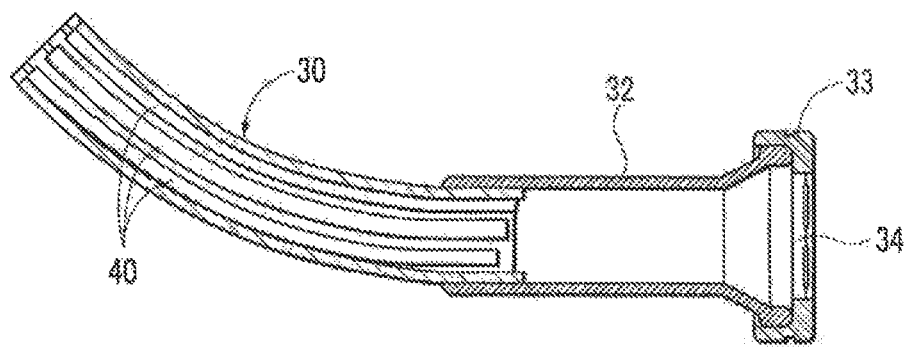
FIG. 3B is a cross-sectional view of a bent outer tube, etc.

The outer tube 30 is composed of soft portions 30A and hard portions 30B alternately coupled to one another in the axial direction as shown in FIGS. 3A and 3B, the soft portions 30A being formed of soft plastic such as polypropylene or vinyl chloride or a soft material such as rubber while the hard portions 30B are harder than the soft portions 30A and formed of hard plastic such as ABS or polycarbonate or a hard material such as hard rubber. However, both the end portions in the axial direction of the outer tube 30 include hard portions 30B. The outer tube 30 may be constructed to be partially or wholly transparent or translucent.

As shown in FIG. 2, a first wire member 51 is embedded in the axial direction from the distal end side to the proximal end side on the peripheral wall portion of the outer tube 30. The first wire member 51 further extends rearwards from the proximal end portion of the outer tube 30, and advance or retreat of the first wire member 51 is operated by a first wire member operating unit (not shown), whereby the outer tube 30 can be bent in the circumferential direction to turn the distal end portion of the outer tube 30 to a desired direction.

The shape of the first wire member 51 may be temporarily fixed by temporarily locking the operation of the first wire member operating unit, for example by a ratchet mechanism, thereby maintaining the state where the distal end portion of the outer tube 30 is turned to the desired direction.

The rail members 40 are formed of a hard material which is the same as or equivalent to the hard material of the hard portions 30B, for example, hard plastic such as ABS or polycarbonate or a hard material such as hard rubber, and constructed as elongated bodies having flexibility. The rail member 40 has a guided portion 41 which extends in the axial direction from the distal end side to the proximal end side on the outer surface thereof. The guided portion 41 is a protrusion formed on the outer surface of the rail member 40. The guided portion 41 may be intermittently formed.

In this embodiment, the protrusion is formed in such a shape engageable with the guiding portion 31 of the outer tube 30, and the outside and neck portion thereof have rectangular cross-sectional shapes. However, the cross-sectional shape of the protrusion is not limited to the foregoing shapes, and may be a substantially trapezoidal shape spreading to the back side, or substantially circular at the outside thereof and rectangular at the neck portion.

The dovetail groove is formed by the inner peripheral surface of the outer tube 30 and the right and left side surfaces of the adjacent rail members 40, and this dovetail groove constitutes an engaging portion 50.

In this embodiment, the dovetail groove has the rectangular cross-sectional view at both the opening portion and the back side as shown in FIG. 2. However, the cross-sectional shape of the dovetail groove may be a substantially trapezoidal shape which spreads further to the back side than the opening portion, or may be rectangular at the opening portion and substantially circular on the back side or the like.

As shown in FIGS. 3A and 3B, the distal end portions of the rail members 40 are fixed to the hard portion 30B nearest to the distal end side of the outer tube 30 by adhesive agent or the like while the guided portions 41 are engaged with the guiding portions 31, but the other portions of the rail members 40 are not fixed to the outer tube 30. As a result, when the outer tube 30 is bent, the respective rail members 40 bend while following the bending of the outer tube 30, and thus the rail members 40 do not hinder the bending of the outer tube 30. Accordingly, the outer tube 30 can be bent while maintaining the cross-sectional shape.

Furthermore, a guide pipe 32, an air leakage preventing ring 33, ad a valve sheet 34 are fitted to the proximal end side of the outer tube 30.

The guide pipe 32 is a member for connecting the outer tube 30 and the air leakage preventing ring 33, and formed of metal such as stainless steel or the like, or a hard material such as resin. The air leakage preventing ring 33 is adhesively fixed to the valve sheet 34. The air leakage preventing ring is detachably fitted to the guide pipe 32. Plural holes through which the inner tubes 20 are inserted are formed in the valve sheet 34.

As shown in FIG. 2, the inner tube 20 is a cylindrical body having flexibility, and a treatment instrument such as an endoscope, forceps or a surgical knife is insertable into the inner tube 20. The inner tube 20 may have one channel for inserting the treatment instrument or two or more channels. The outer peripheral surface of the inner tube 20 may be subjected to a hydrophilic treatment. According to hand manipulation, each inner tube 20 can be inserted into and removed from the outer tube 30 whose inner peripheral surface is engaged with the rail members 40.

In this embodiment, the inner tubes 20 have the same outer diameter, but the inner tubes 20 having different outer diameters may be used.

Figure 4B:
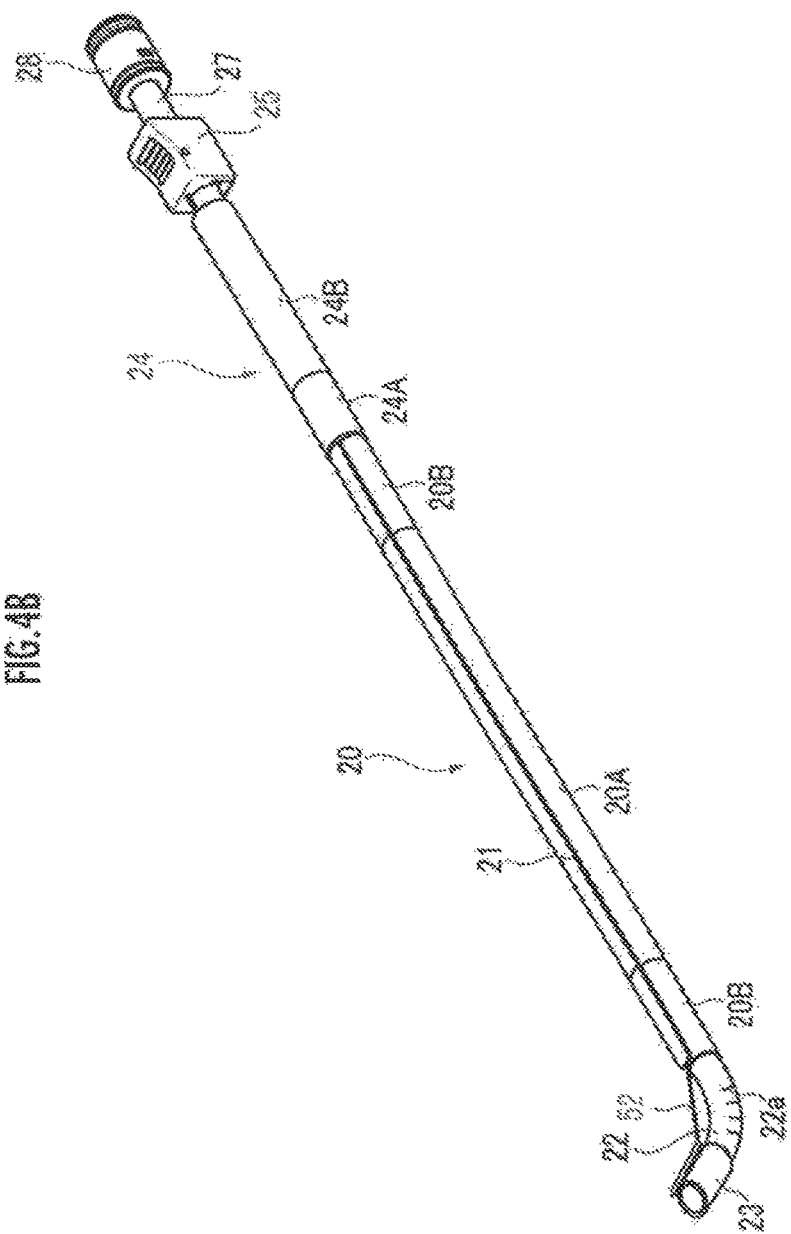
FIG. 4B is a perspective view of a bent inner tube of FIG. 4A, etc.

As shown in FIGS. 4A and 4B, the inner tube 20 is composed of soft portions 20A and hard portions 20B coupled to one another in the axial direction, the soft portions 20A being formed of soft plastic such as polypropylene or vinyl chloride or a soft material such as rubber while the hard portions 20B are harder than the soft portions 20A and formed of hard plastic such as ABS or polycarbonate or a hard material such as hard rubber. Both the end portions in the axial direction of the inner tube 20 include hard portions 20B, and an intermediate portion between these hard portions 20B includes a soft portion 20A.

Referring also to FIG. 2, the inner tube 20 has an engaged portion 21 which is slidably engageable with an engaging portion 50 from the distal end to the proximal end of the outer peripheral surface of the inner tube 20, and a scale (not shown) for grasping the insertion depth.

In this embodiment, the engaged portion 21 is a rectangular wide protrusion protruding to the outer peripheral surface of the inner tube 20, but it has any shape insofar as it is engageable with the engaging portion 50.

The engaged portion 21 is continuously provided from the distal end to the proximal end of the inner tube 20. However, the engaged portion 21 may be intermittently provided at a part of the portion between the distal end and the proximal end of the outer peripheral surface of the inner tube 20, and may be provided at least only at the distal end.

A second wire member 52 is embedded in the axial direction from the distal end side to the proximal end side in the engaged portion 21 of the inner tube 20. The second wire member 52 further extends rearwards from the proximal end portion of the inner tube 20, and advance and retreat thereof can be performed by a slide knob 25 (an operating unit for the second wire member). The second wire member 52 may be merely fixed to the inner tube 20, and it may be embedded on the peripheral wall portion of the inner tube 20 instead of being embedded in the engaged portion 21, or adhesively fixed to the outer peripheral surface of the inner tube 20.

A bendable swing pipe (corresponding to a bending member of the present invention) 22 and a nose cover 23 (corresponding to a cover of the present invention, and see FIGS. 4A and 4B) are fitted to the distal end portion of the inner tube 20.

The swing pipe 22 is formed of a hard material whose hardness is equal to or harder than that of the hard portion 20A of the inner tube 20, for example, metal such as stainless steel or the like. Plural slits 22a extending in the axial direction are formed in the swing pipe 22. In this embodiment, a thin wall part(s) may be formed in place of formation of the slits 22a. As a result, the swing pipe 22 is easily bendable only in a specific direction. The second wire member 52 passes outside the swing pipe.

The nose cover 23 is fixed to the distal end portion of the swing pipe 22. The nose cover 23 is formed of a soft material softer than the hard material constituting the swing pipe 22, for example, soft plastic such as vinyl chloride, rubber or the like. Since the nose cover 23 is formed of the soft material, the nose cover 23 does not damage tissues even when it comes into contact with the tissues. The distal end portion of the second wire member 52 is fixed to the nose cover 23.

On the other hand, a first slide pipe 24, a slide knob 25, a slide stopper 26, a second slide pipe 27 and a deaeration preventing valve 28 are fitted to the proximal end portion of the inner tube 20.

The first slide pipe 24 is connected to the rear end portion of the inner tube 20, and inserted in the air leakage preventing ring 33 (see FIGS. 3A and 3B). As a result, air in a body cavity can be prevented from leaking from places where the inner tubes 20 of the outer tube 30 are not inserted, or from the outer peripheral portions of the inserted inner tubes 20.

The distal end side of the first slide pipe 24 includes a hard portion 24A formed of a hard material whose hardness is equal or equivalent to the hardness of the hard portion 20B of the inner tube 20, and the rear end side of the first slide pipe 24 includes a semi-hard portion 24B formed of a semi-hard material such as elastomer, polyurethane or the like whose hardness is softer than the hard portion 20B of the inner tube 20 and harder than the soft portion 20A. When the plural inner tubes 20 are inserted into the outer tube 30, the semi-hard portions 24B can prevent the interference among the inner tubes 20.

The rear end portion of the second wire member 52 is fixed to the slide knob 25. The slide knob 25 is constructed to be freely slidable with respect to the second slide pipe 27, and can be locked at a desired position with respect to the second slide pipe 27 by the slide stopper 26.

The deaeration preventing valve 28 can prevent occurrence of air leakage from a body cavity, for example, an abdominal cavity from the inner tubes 20 in which no treatment instrument is inserted. The deaeration preventing valve 28 is freely detachably fitted to the rear end of the second slide pipe 27.

When the distal end portion of the inner tube 20 protrudes from the distal end of the outer tube 30, the second wire member 52 bends the swing pipe 22 to turn the distal end portion of the swing pipe 22 to a desired direction. When the distal end portion of the inner tube 20 does not protrude from the distal end of the outer tube 30 and the inner tube 20 is accommodated in the outer tube 30, the second wire member 52 can bend the outer tube 30 while following bending of the inner tube 20.

The shape of the second wire member 52 may be temporarily fixed by temporarily locking the operation of the slide knob 25, for example by a ratchet mechanism, thereby maintaining the state where the distal end portion of the inner tube 20 or the outer tube 30 is turned to a desired direction.

Engaged portions 61 of guide members 60 are engaged with the engaging portions 50 with which the engaged portions 21 of the inner tubes 20 are not engaged.

Figure 5A:
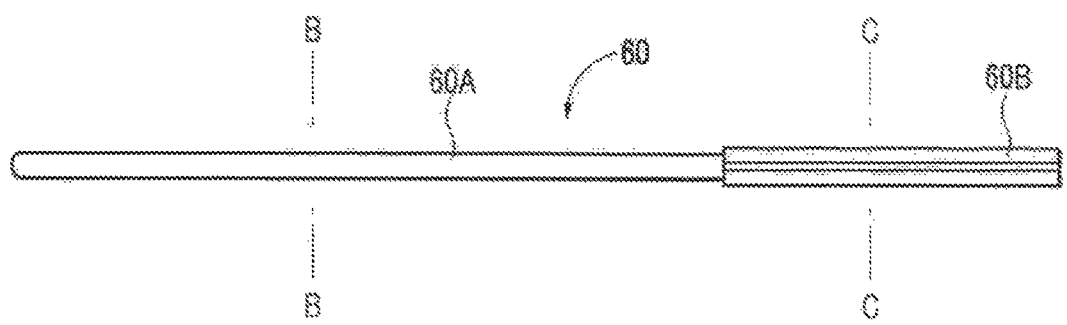
FIG. 5A is a side view of a guide member.
Figure 5B:
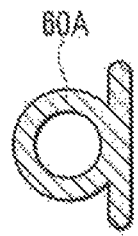
FIG. 5B is a cross-sectional view taken along a B-B line of FIG. 5A.
Figure 5C:
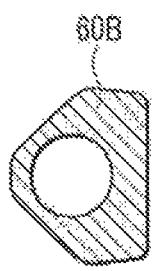
FIG. 5C is a cross-sectional view taken along a C-C line of FIG. 5A.

As shown in FIGS. 5A to 5C, the guide member 60 is an elongated member including a distal end side portion 60A at which the engaged portion 61 to be engaged with the engaging portion 50 is formed inside, and a proximal end side portion 60B. The distal end side portion 60A is formed of a semi-hard material such as elastomer, polyurethane, a wire or a copper wire which is softer than the hard portion 20B of the inner tube 20 and harder than the soft portion 20A. The proximal end side portion 60B is formed of a hard material whose hardness is equal or equivalent to the hard portion 20B of the inner tube 20.

In this embodiment, the engaged portion 61 is a rectangular wide protrusion protruding to the outer peripheral surface of the inner tube 20, but it may have any shape insofar as it is engageable with the engaging portion 50. The main body portion 62 of the distal end side portion 60A has a toroidal cross-section. The proximal end side portion 60B has a substantially triangular cross-section having a circular hole at an apex thereof.

According to the treatment-instrument insertion aid 10 of this embodiment, the engaged portions 21 of the inner tubes 20 are slid while engaged with the guiding portions 31 extending in the axial direction from the distal end side to the proximal end side, whereby the inner tubes 20 can be smoothly inserted and pulled out while maintaining the positions of the inner tubes 20 in the outer tube 30, and a desired treatment instrument can be used.

As described above, according to the treatment-instrument insertion aid 10 of this embodiment, since both the end portions of the inner tube 20 include the hard portions 20B, the inner tube 20 can be prevented from being crushed at both the end portions thereof. Furthermore, since the intermediate portion of the inner tube 20 includes the easily bendable soft portion 20A, the inner tube can be easily bent during hand manipulation.

Since the swing pipe 22 is fitted to the distal end portion of the inner tube 20, the treatment instrument can be easily turned to a desired direction.

Furthermore, since the nose cover 23 formed of the soft material is fitted to the distal end portion of the swing pipe 22, a risk of damaging tissues can be prevented.

Since both the end portions of the outer tube 30 include the hard portions 30B, the outer tube 30 can be prevented from being crushed at least at both the end portions, and further the inner tubes 20 of the outer tube 30 can be prevented from being crushed. Since the outer tube 30 has the easily bendable soft portions 30A, the outer tube 30 can be easily bent during hand manipulation.

In addition, since the hard portion 30B also exists at the intermediate portion, the outer tube 30 can be also prevented from being crushed at this portion. Furthermore, the inner tubes 20 in the outer tube 30 can be more effectively prevented from being crushed.

Furthermore, since the inner tubes 20 can be locked at predetermined places by using the rail members 40 locked on the inner peripheral surface of the outer tube 30, the interference among the inner tubes 20 can be prevented.

Since the guide members 60 are engaged with the engaging portions 50 with which no inner tube 20 is engaged, the interference among the inner tubes 20 can be surely prevented by the guide members 60.

The embodiment of the present invention has been described above. However, the present invention is not limited to the above embodiment, and the configuration and form of the assembled device may be appropriately modified.

For example, in the foregoing description, the plural rail members 40 are engaged with the inner peripheral surface of the outer tube 30 to configure the engaging portions 50. However, the present invention is not limited to this configuration, and the outer tube 30 and the plural rail members 40 may be integrated with each other to configure the engaging portions 50. Furthermore, the soft material, the hard material and the semi-hard material may be materials obtained by changing the blending of the same kind of resin to adjust softness and hardness.

REFERENCE SIGNS LIST

10 . . . treatment-instrument insertion aid, 20 . . . inner tube, 20A . . . soft portion (intermediate portion), 20B . . . hard portion (both end portions), 21 . . . engaged portion, 22 . . . swing pipe (bending member), 22a . . . slit, 23 . . . nose cover (cover), 30 . . . outer tube, 30A . . . soft portion, 30B . . . hard portion, 31 . . . guiding portion, 40 . . . rail member, 41 . . . guided portion, 50 . . . engaging portion, 51 . . . first wire member, 52 . . . second wire member, 60 . . . guide member, 61 . . . engaged portion

The invention claimed is:

1. A treatment-instrument insertion aid for aiding insertion of a treatment instrument into a body, comprising:
an inner tube having flexibility into which the treatment instrument is insertable; and
an outer tube having flexibility into which an entirety of the inner tube is insertable,
wherein
both end portions of the inner tube are formed of a hard material, and an intermediate portion of the inner tube between the both end portions is formed of a soft material softer than the hard material,
an engaging portion is provided on an inner peripheral surface of the outer tube, and an engaged portion to be engaged with the engaging portion is provided on an outer peripheral surface of the inner tube,
the engaging portion is engaged with the engaged portion to attach the inner tube in a state of being inserted inside the outer tube,
a bendable bending member having a cylindrical shape is attached to a distal end of the inner tube,
a plurality of guiding portions are provided circumferentially spaced apart from one another on an inner peripheral surface of the outer tube,
a plurality of guided portions of a respective plurality of rail members each extending in an axial direction from a distal end side to a proximal end side are respectively engaged with the plurality of guiding portions, and
the engaging portion is formed by the inner peripheral surface of the outer tube and adjacent rail members.

2. The treatment-instrument insertion aid according to claim 1, wherein the bending member is formed of a bending member hard material same as or harder than the hard material, and partially has a thin wall part which is reduced in thickness relative to thickness of other parts of the bending member.

3. The treatment-instrument insertion aid according to claim 2, wherein a cover formed of a cover soft material softer than the bending member hard material is attached to a distal end portion of the bending member.

4. The treatment-instrument insertion aid according to claim 1, wherein both end portions of the outer tube are formed of an outer tube hard material, and an intermediate portion between the both end portions of the outer tube has a portion formed of an outer tube soft material softer than the outer tube hard material.

5. The treatment-instrument insertion aid according to claim 4, wherein the intermediate portion of the outer tube has alternately a portion formed of the outer tube soft material and a portion formed of the outer tube hard material harder than the outer tube soft material.

6. The treatment-instrument insertion aid according to claim 1, wherein
- a plurality of the engaging portion are provided circumferentially spaced apart from one another on the inner peripheral surface of the outer tube,
- the inner tube is provided with the engaged portion on the outer peripheral surface thereof to be engaged with one of the plurality of the engaging portion,
- the number of inner tube provided is at least one less than a number of the plurality of the engaging portion, and
- an engaged portion of a guide member extending in the axial direction from the distal end side to the proximal end side is engaged with another one of the plurality of the engaging portion with which the engaged portion of the inner tube is not engaged.

7. The treatment-instrument insertion aid according to claim 1, wherein the engaging portion is engaged with the engaged portion to attach the inner tube to the outer tube with the inner tube inserted inside the outer tube.

8. The treatment-instrument insertion aid according to claim 1, wherein the engaging portion is engaged with the engaged portion to attach the inner tube to the outer tube with the entirety of the inner tube inserted inside the outer tube.

* * * * *